United States Patent [19]

Heilman et al.

[11] Patent Number: 4,928,690

[45] Date of Patent: May 29, 1990

[54] PORTABLE DEVICE FOR SENSING CARDIAC FUNCTION AND AUTOMATICALLY DELIVERING ELECTRICAL THERAPY

[75] Inventors: Marlin S. Heilman, Sarver; Arlan J. Brandt, Gibsonia; Larry D. Bowling; Joseph F. Russial, both of Pittsburgh, all of Pa.

[73] Assignee: Lifecor, Inc., Pittsburgh, Pa.

[21] Appl. No.: 185,781

[22] Filed: Apr. 25, 1988

[51] Int. Cl.$^5$ .............................................. A61N 1/00
[52] U.S. Cl. .................................. 128/421; 128/702; 128/419 D; 128/696
[58] Field of Search ........ 128/419 D, 419 P, 419 PG, 128/421, 696, 702

[56] References Cited

U.S. PATENT DOCUMENTS

| | | | |
|---|---|---|---|
| 3,241,556 | 3/1966 | Zacouto | 128/421 |
| 3,460,542 | 8/1969 | Gemmer | 128/421 |
| 3,702,613 | 11/1972 | Panico et al. | 128/417 |
| 3,826,245 | 7/1974 | Funfstuck | 128/206 |
| 3,942,533 | 3/1976 | Cannon, III | 128/417 |
| 3,961,623 | 6/1976 | Milani et al. | 128/206 |
| 4,002,239 | 1/1977 | Buchalter | 206/484 |
| 4,058,127 | 11/1977 | Buchalter | 128/417 |
| 4,088,138 | 5/1978 | Diack et al. | 128/419 D |
| 4,576,170 | 3/1986 | Bradley et al. | 128/419 D |
| 4,729,377 | 3/1988 | Granek et al. | 128/639 |

Primary Examiner—Francis Jaworski
Assistant Examiner—George Manuel
Attorney, Agent, or Firm—Fleit, Jacobson, Cohn, Price, Holman & Stern

[57] ABSTRACT

A patient-worn harness or vest protects at-risk patients from the possibly fatal results of heart arrhythmias. The harness or vest incorporates sensing electrodes for monitoring heart condition, a microprocessor and memory for processing signals received from the sending electrodes and comparing same with patient's data, and skin-contacting pulsing electrodes for applying electrical pulses to the patient's chest wall responsive to signals received from the microprocessor. The electrodes include automatic tightening and electrolyte gel release mechanisms for reducing impedance at the electrode-skin interface. A servicing subsystem is provided for the harness or vest and may be used to interface with the harness or vest and also to communicate with remote health care personnel through a suitable telephone link.

51 Claims, 15 Drawing Sheets

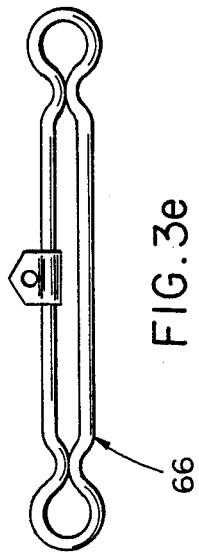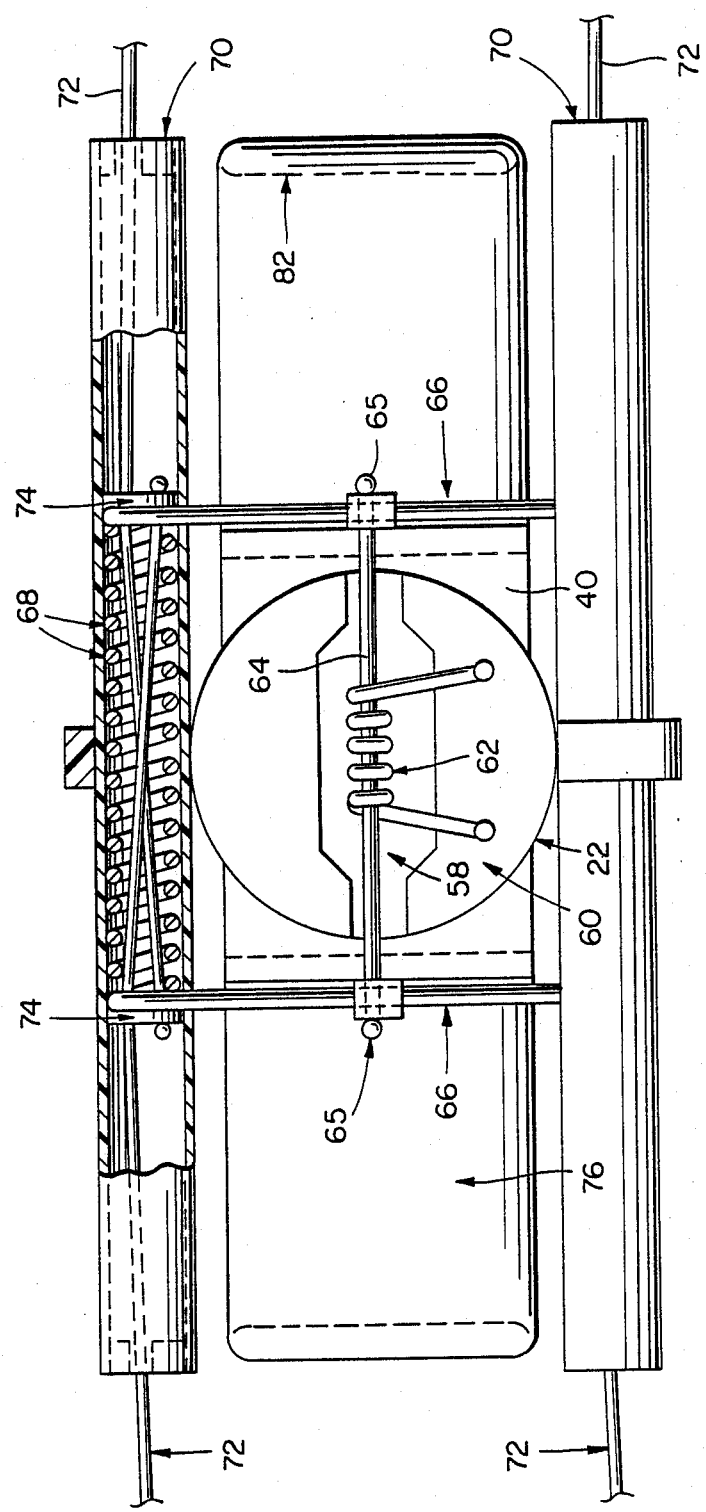

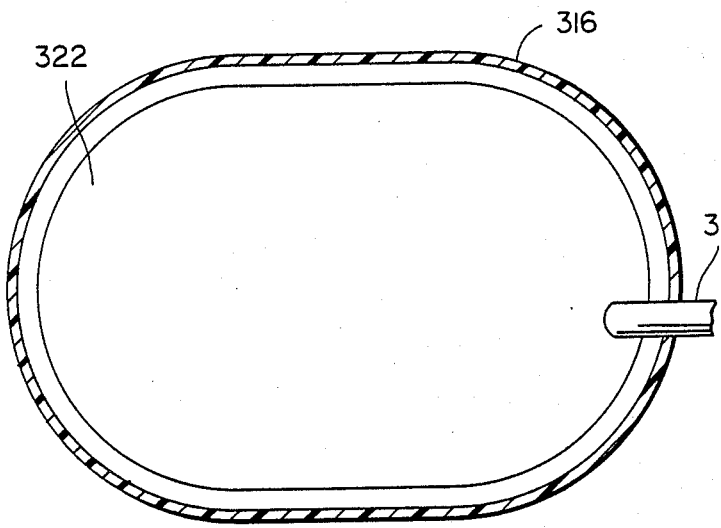
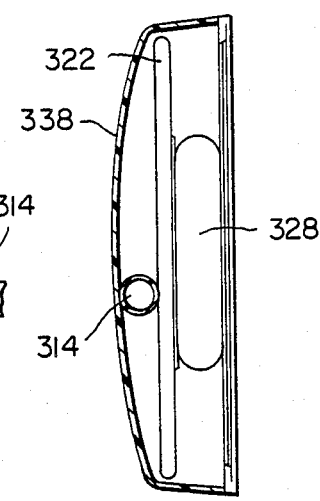
FIG.15a  FIG.15b
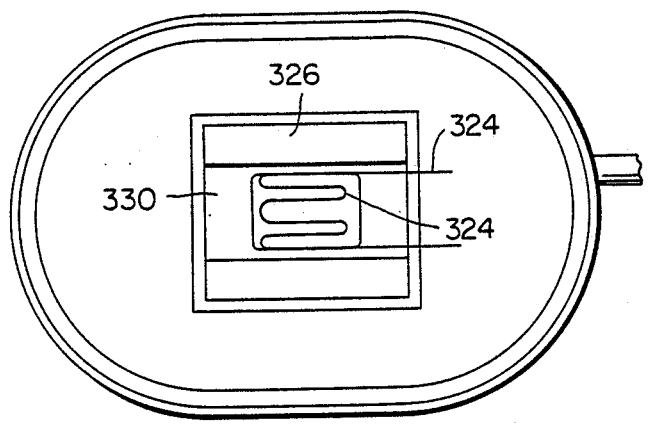
FIG.15c
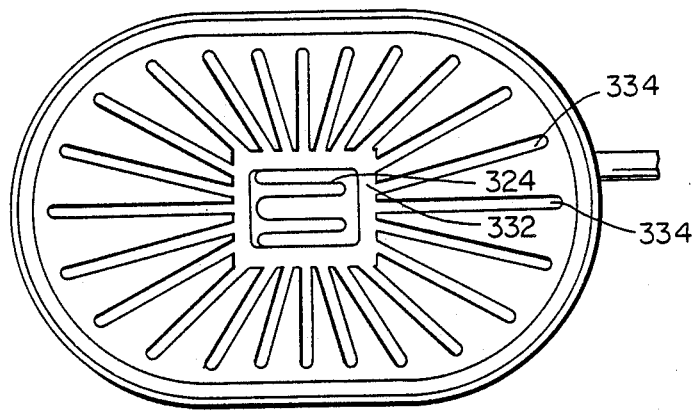
FIG.15d

PORTABLE DEVICE FOR SENSING CARDIAC FUNCTION AND AUTOMATICALLY DELIVERING ELECTRICAL THERAPY

FIELD OF THE INVENTION

This invention relates generally to the treatment of human heart defects by the administration of electrical therapy. More particularly, the invention relates to a system and means for protecting susceptible or at-risk patients from sudden death due to excessively fast or slow heart rates.

BACKGROUND OF THE INVENTION

For several years, technology has been available for correcting excessively slow heart rates (bradycardia) by implantable devices, commonly referred to as pacemakers, which deliver microjoule electrical pulses to a slowly beating heart in order to speed the heart rate up to an acceptable level. Also, it is well known to deliver high energy shocks (180 to 360 joules) via external paddles applied to the chest wall in order to correct excessively fast heart rates and prevent the possible fatal outcome of ventricular fibrillation or certain ventricular tachycardias. Bradycardia, ventricular fibrillation and ventricular tachycardia are all electrical malfunctions (arrhythmias) of the heart and each may lead to death within minutes unless corrected by the appropriate electrical stimulation.

Because time delays in applying the corrective electrical treatment may result in death, implantable pacemakers and defibrillators have significantly improved the ability to treat these otherwise life threatening conditions. Being implanted within the patient, the device continuously monitors the patient's heart for treatable arrhythmias and when such is detected, the device applies corrective electrical pulses directly to the heart.

Pacemakers and defibrillators that apply corrective electrical pulses externally to the patient's chest wall also are used to correct such life-threatening arrhythmias but suffer from a drawback insofar as it may not be possible to apply the device in time during an acute arrhythmic emergency to save the patient's life. Such treatment is needed within a few minutes to be effective. Consequently, when a patient is deemed at high risk of death from such arrhythmias, the electrical devices are implanted so as to be readily available when treatment is needed. Alternatively, such patients are kept in a hospital where corrective electrical therapy is generally close at hand. Long term hospitalization, however, is frequently impractical due to its high cost or due to the requirements for patients to engage in normal daily activities.

There are also many patients susceptible to heart arrhythmias who are at temporary risk of sudden death. For example, patients undergoing a coronary artery occlusion and myocardial infarction are at substantial risk of tachyarrhythmias for several weeks following the coronary artery occlusion. Such patients are generally hospitalized but could be discharged earlier if there was a practical means to protect them from life threatening arrhythmias. There are also numerous patients awaiting implantation of an automatic defibrillator who require an external defibrillator to be close at hand in case they experience a life-threatening tachyarrhythmia. Additionally, there are patients in need of an implantable defibrillator who are placed at inordinate risk due to the surgery required for implanting such a device.

It is evident from the above that there is a real need for providing an effective means whereby susceptible patients can be protected on a relatively long-term basis against the dangerous consequences of an electrical heart malfunction without having to undergo an implant procedure and without having to remain hospitalized.

SUMMARY OF THE INVENTION

It is an object of the invention to provide a system and means as referred to above, whereby a patient susceptible to certain heart arrhythmias can be effectively protected against harmful consequences resulting therefrom without having to undergo an implant procedure and without having to remain hospitalized.

Another object of the invention is to provide an effective form of externally applied electrical therapy which can provide relatively long-term protection to a patient against the consequences of heart arrhythmias without the patient having to forego normal everyday activities.

The present invention provides a system and means whereby susceptible patients may be substantially protected from arrhythmic death including a portable patient-worn external pacemaker/defibrillator that is comfortable to wear yet has the capability of continuously monitoring the patient for potentially lethal arrhythmias and delivering corrective electrical pulses quickly and appropriately in the event that such arrhythmia occurs. The invention also provides a supportive non-patient-worn system and means to optimize the operational readiness and reliability of the patient-worn device. Emphasis in the present inventive system and means is placed on optimizing reliable operation and further on maximizing patient compliance in wearing such a device by making the device comfortable and user compatible.

Further, according to the present invention, there are provided a number of means whereby the automatic external pacemaker/defibrillator may be worn comfortably by an at-risk patient. Included are means to minimize the weight of the device, means to distribute the weight-bearing surfaces over a large body area, means to allow the device to be loosely fitting in a standby mode, and means to allow a comfortable undergarment to be generally positioned between the device and the patient's skin. Most importantly, the device also includes means to cause a low impedance pathway to be established for an electrical pulse to the heart when a potentially dangerous arrhythmia has been detected by the device.

Correct reliable positive detection of arrhythmias and minimal false detections are important to the utility of the wearable anti-arrhythmic device. Accordingly, it is also preferred that the device continuously monitor more than one physiological indicator of a treatable arrhythmia. Since various types of patient behavior may produce unreliable detection, means may be provided for advising the patient of the status of the detection circuits such that the patient may learn behavior patterns that optimize reliable device operation The device may also include means whereby the patient may delay the delivery of a high energy shock if conscious, indicating that the arrhythmia is not yet life-threatening.

It is a further object of the invention to provide different types of system monitoring means to maximize safety, efficacy and reliability of the patient-worn device. Such monitoring means may include means to check operational readiness of the patient-worn device, means to check battery status of the device, means to recharge the batteries if necessary, means to record memory contents of the patient-worn device, and means to transmit vital data to remote health care personnel for problem solving and advising on correct device operation.

The above and other objects that will hereinafter appear, and the nature of the invention, will be more clearly understood by reference to the following description, the appended claims and the accompanying drawings.

BRIEF DESCRIPTION OF THE DRAWINGS

FIG. 3d is an enlarged plan view, partly broken away, of the interior of the electrode assembly with the cover removed;

FIG. 3e is an end elevational view of one of the electrode components;

FIGS. 15a and 15b are respectively a plan view and an end view of an electrode housing with a gas source remotely mounted;

FIGS. 15c and 15d are respective bottom views of the electrode housing, with a fluid container, resistive heating element and retaining member being shown with channels being removed in FIG. 15c and being in place in FIG. 15d;

DETAILED DESCRIPTION OF THE PREFERRED EMBODIMENT

Figure 4:
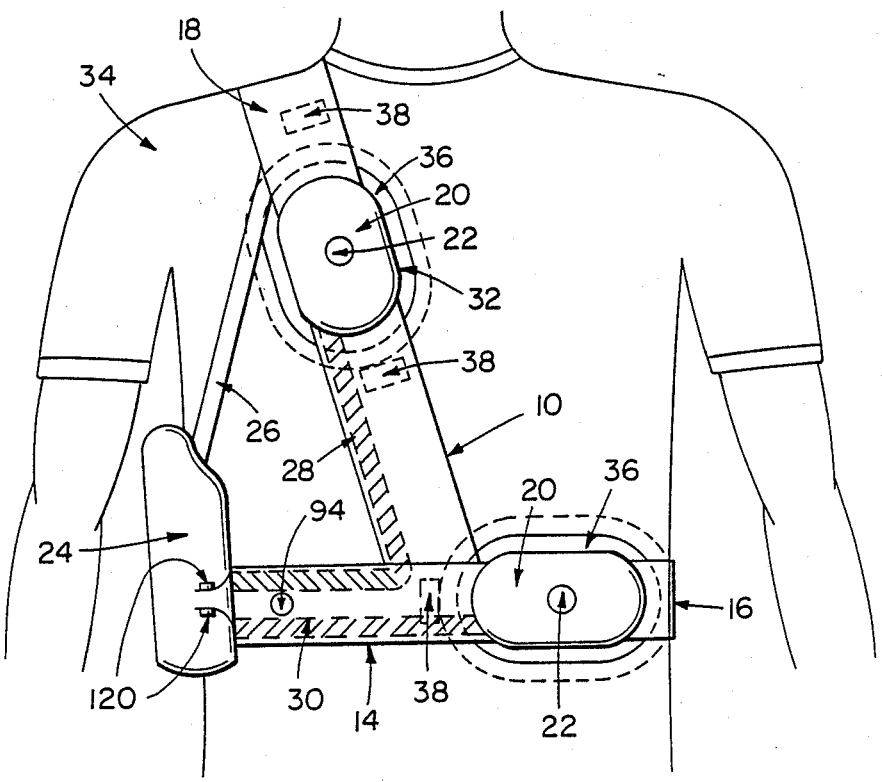
FIG. 4 is a diagrammatic in-use view of the first embodiment pacemaker/defibrillator as worn by a patient.
Figure 6:
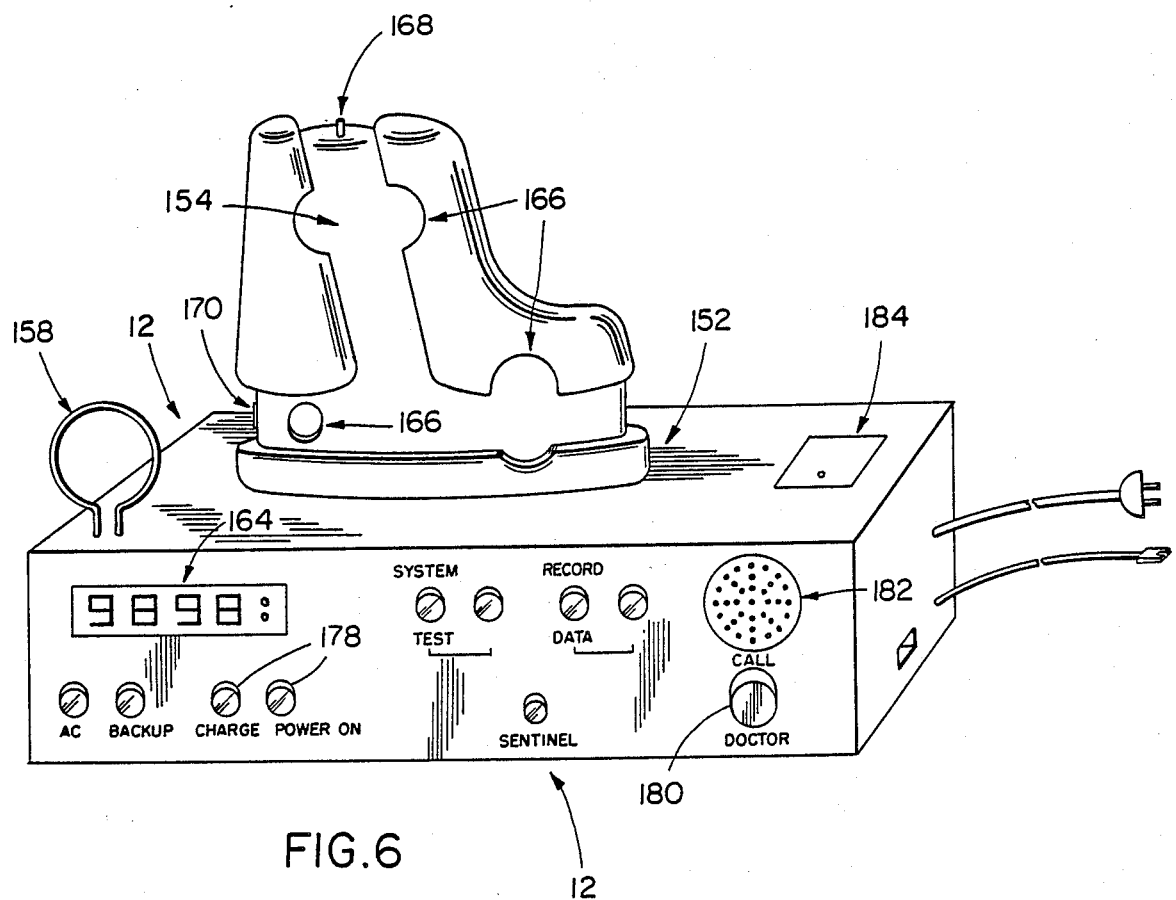
FIG. 6 is a diagrammatic perspective view of the maintenance subsystem.
Figure 7:
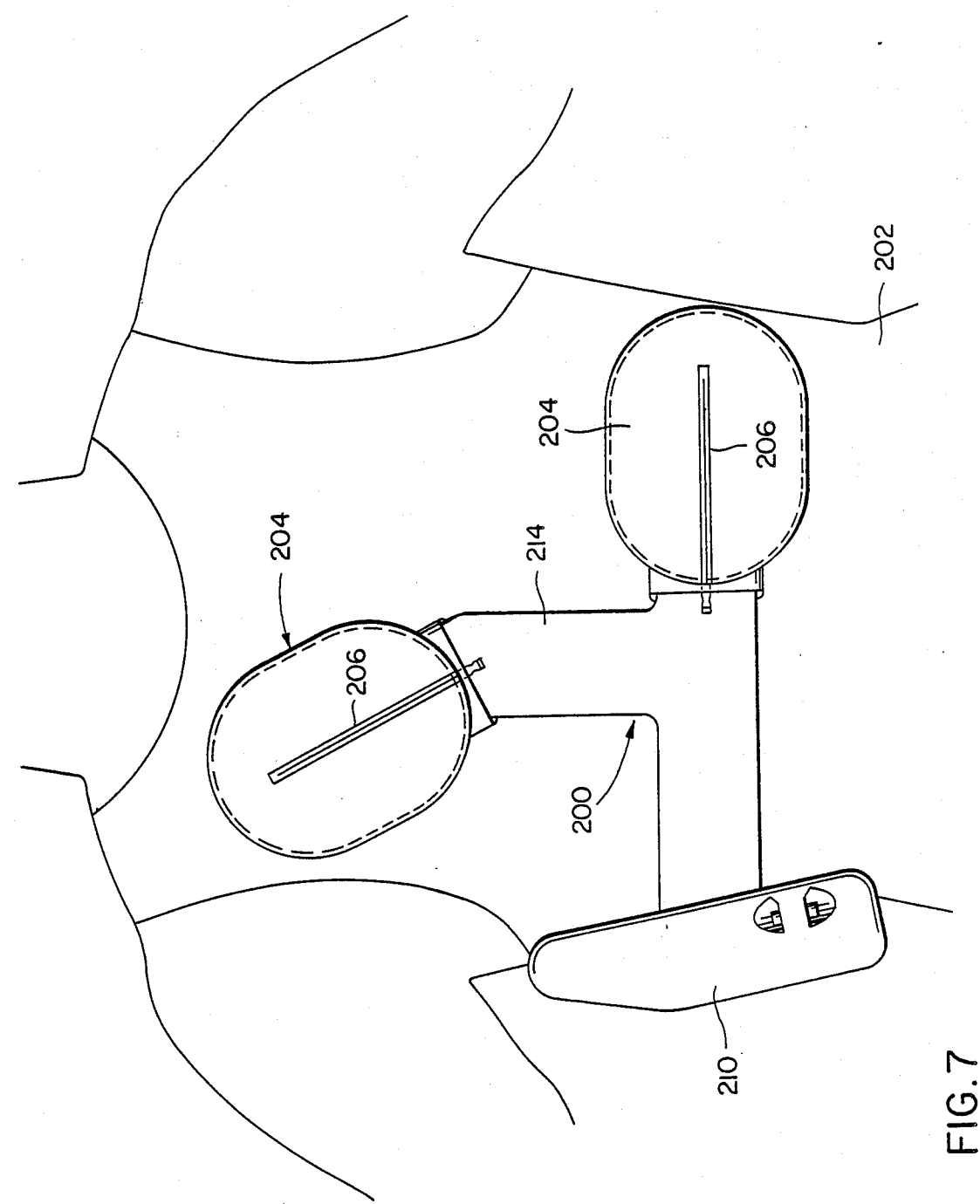
FIG. 7 is a diagrammatic in-use view of a second embodiment pacemaker/defibrillator device in accordance with the invention, shown in association with an upper-body garment with which it is worn.
Figure 8:
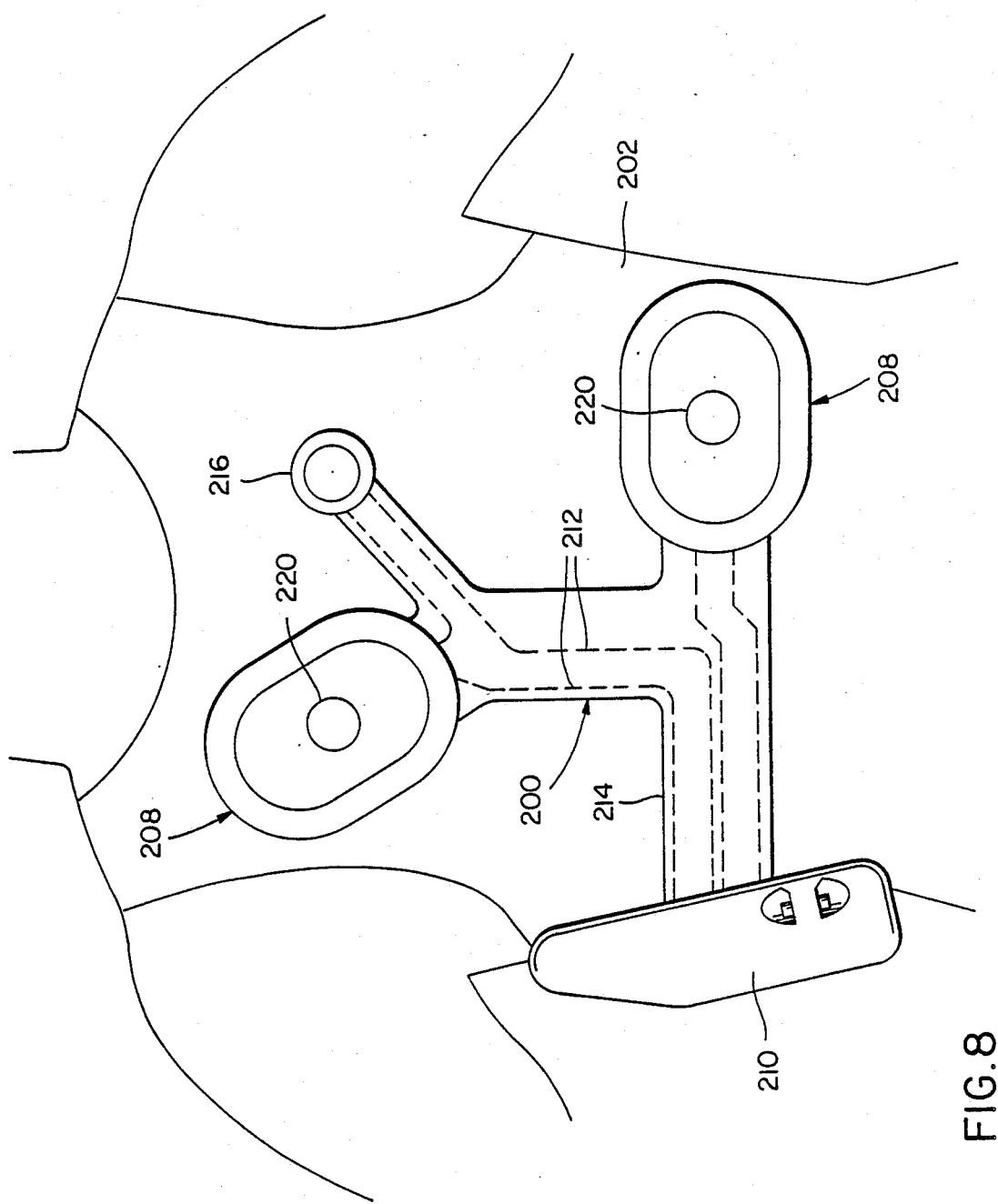
FIG. 8 is a view of the second embodiment pacemaker/defibrillator device in it in-use position, and shown in somewhat more detail.

Generally stated, in a preferred form of the invention as illustrated in the drawings, there is provided a patient-wearable automatic electric heart therapy device, such as device 10, shown in overall view in FIG. 4, or device 200 shown in overall view in FIGS. 7 and 8, and a maintenance subsystem or module 12, shown in overall view in FIG. 6 on which the respective therapy device 10 or 200 can be mounted when not in use on a patient, effectively to service, program and charge the device.

As shown in FIG. 4, in a first embodiment, the patient-worn device may include a waist-encompassing belt 14 of suitable fabric, webbing or the like, which may be elasticized, or may incorporate sprung elements the belt having a low-profile connector or buckle 16, and a shoulder strap 18 of like material connected between front and rear portions of the belt. First and second like sensing and pulse electrode assemblies 20 are carried respectively on belt 14 and shoulder strap 18. Belt 14 also carries a pulse generator 24 which may have a supporting strap connection 26 with strap 18 and electrical conductors, diagrammatically indicated at 28 and 30, for receiving electrical signals from and delivering electrical pulses to the respective electrode assemblies 20. Assemblies 20 have respective sensing electrodes 22 and pulse electrodes 32.

In use of the device as thus far described, assemblies 20 are held in comfortable contact with a patient's chest wall and continuously monitor and detect the heart rhythm by means of the respective sensing electrodes 22. Alternatively, sensing electrodes may be traditional disposable E.C.G. electrodes placed on the patient's skin in a location separate from the pulse electrodes 32. In the event that the sensing electrodes detect a treatable heart arrhythmia, the electrodes will send the sensed signal via conductors 28 and 30 to the pulse generator, and in response thereto, the pulse generator will return appropriate treatment pulses to the respective pulse electrodes 32. Moreover, each of the electrode assemblies further includes means (to be described below) for automatically reducing the impedance of electrical transmission to the heart upon receipt of the appropriate treatment commencing signal from the pulse generator. Such impedance reducing means may include, for example, means for automatically tightening the respective pulsing electrodes 32 against the patient's skin, and means for automatically releasing an electrolytic electrode gel to the electrode-skin interface.

Reverting to FIG. 4, it is seen that device 10 may be worn over a comfortable undergarment 34, such as a T-shirt, which may have apertures 36 that receive the respective electrode assemblies 20. Attachments 38, such as patches of loop and pile Velcro-type fabric, may be provided between belt 14, strap 18 and the undergarment.

Figure 2A:
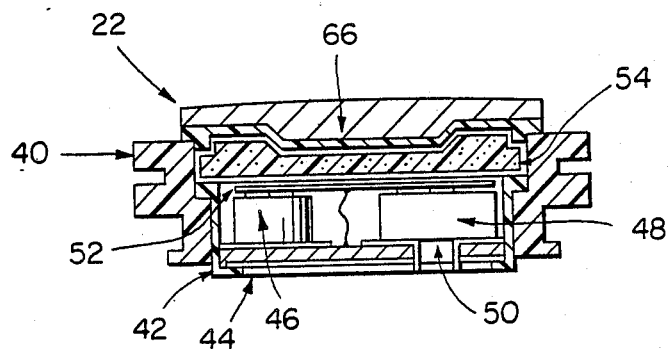
FIG. 2a is a diagrammatic sectional elevational view of a first embodiment combination ECG electrode/heart sound microphone used with the pacemaker/defibrillator device for heart beat detection.
Figure 2B:
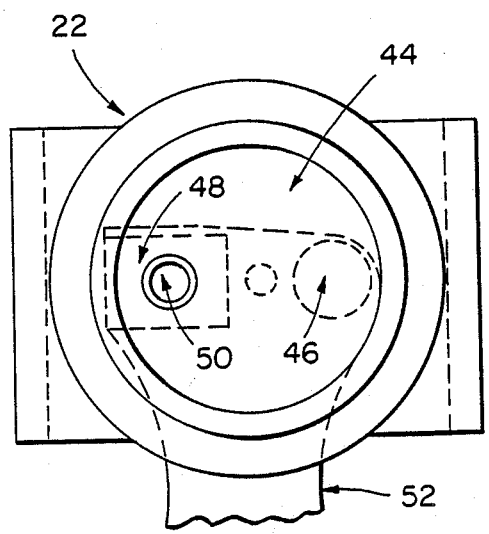
FIG. 2b is an underneath plan view of the microphone.

FIGS. 2a and 2b illustrate details of the respective sensing electrodes 22. Each sensing electrode, which is centrally located in its respective assembly 20, comprises a plastic, cylindrical housing 40 containing a telescoping inner chamber 42 which carries an ECG electrode 44, an associated amplifier 46, and an audio transducer or microphone 48. The ECG electrode 44 may be capacitive, conductive carbon, or any other design which permits long-term use without skin irritation. The microphone is acoustically coupled to a port 50 which conducts audio-frequency energy to the microphone diaphragm. The diameter of the inner chamber is typically about 2.5 cm. Installed over the amplifier 46 and microphone 48, and electrically connected thereto, is a flexible printed circuit 52 supplying power to and receiving signals from the amplifier and microphone. It is understood that the printed circuits of the respective electrodes are connected to the pulse generator 24 through conductors 28 and 30 referred to in connection with FIG. 4.

The inner chamber 42 telescopes within the outer chamber 40 and a synthetic expanded foam pad 54 located beneath a chamber cover 60 applies pressure to the top of the inner chamber and thus to the skin surface, insuring constant contact between the ECG electrode surface and the skin whenever the system is worn.

Figure 3C:
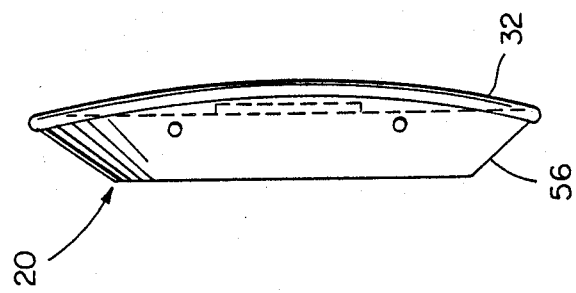
FIG. 3c is an end elevational view of the electrode assembly; p
Figure 3A:
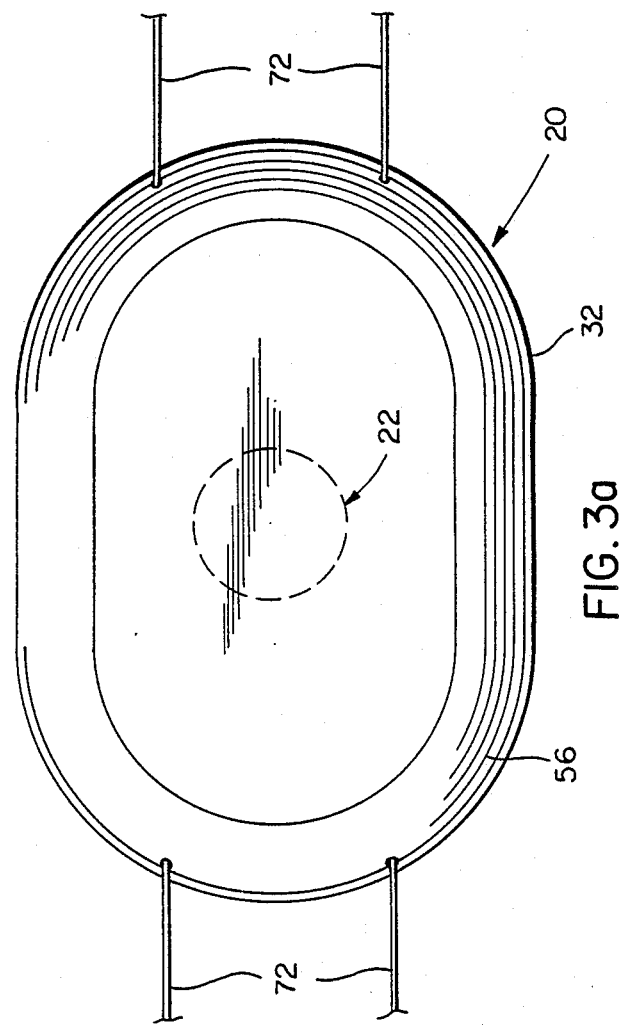
FIG. 3a is a plan view of a first embodiment sensing and pulsing electrode assembly used in the defibrillator device.
Figure 3B:
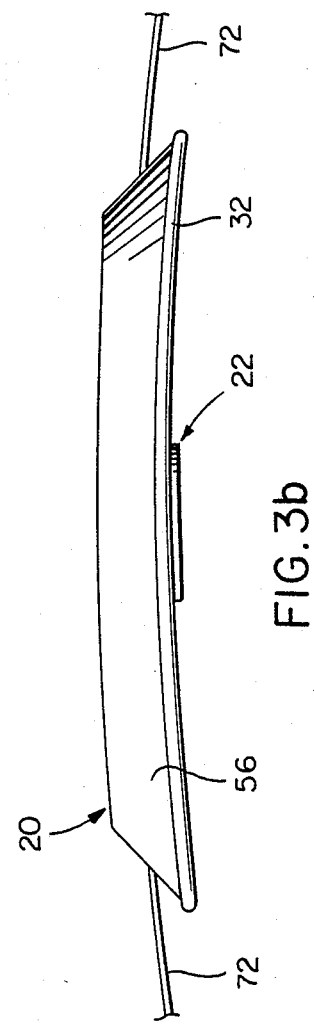
FIG. 3b is a side elevational view of the electrode assembly.
Figure 3F:
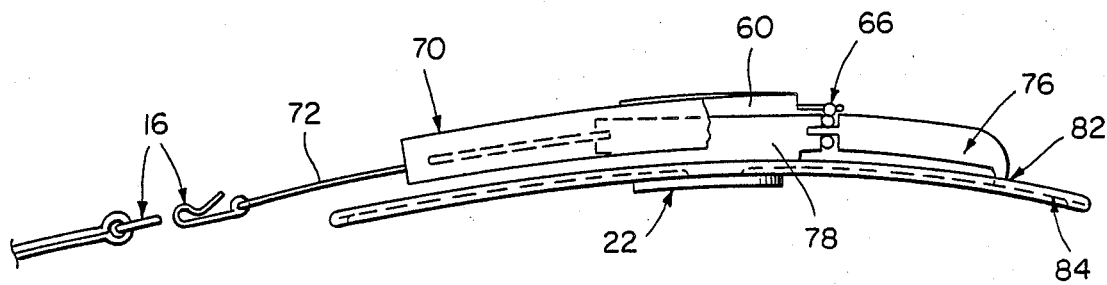
FIG. 3f is a side elevational view of the electrode assembly with the cover removed.

FIGS. 3a-3c illustrate the overall outer appearance and dimensions of the respective electrode assemblies 20, showing the placement of the sensing electrode 22 within the pulse electrode 32. The electrode assemblies each have an outer housing 56 of a flexible, composite material having a skin contact area of approximately 100 square centimeters.

FIGS. 3d-3g illustrate the interior of the respective electrode assemblies with the housing removed. The respective sensing electrode 22 fits centrally within the respective pulse electrode and has a recess 58 provided in the top surface of the central chamber cover 60. Recess 58 contains an electrically-operated release or trigger mechanism, consisting of a heating coil of resistance wire 62 wound around a synthetic fiber activator member 64. Member 64 has headed ends 65 which attach to and retain two spring-loaded equalizer bars and allowing springs 68 to exert force upon the bars which travel within two cantilevered tubes 70. Contained within tube 70 are synthetic fiber tension members 72, fastened at their ends to washers 74 and at their other ends, not shown, into the structure of belt 14 or strap 18 as the case may be. Thus, as the equalizer bars travel within the tubes, the tension members 72, by virtue of their attachment to the washers, are pulled through the tubes, applying tension to the ends of the belt 14 or strap 18 to which the respective electrode housing fastens, thereby tightening the electrode assembly against the patient's skin and providing a firm form of impedance reducing means.

Figure 3G:
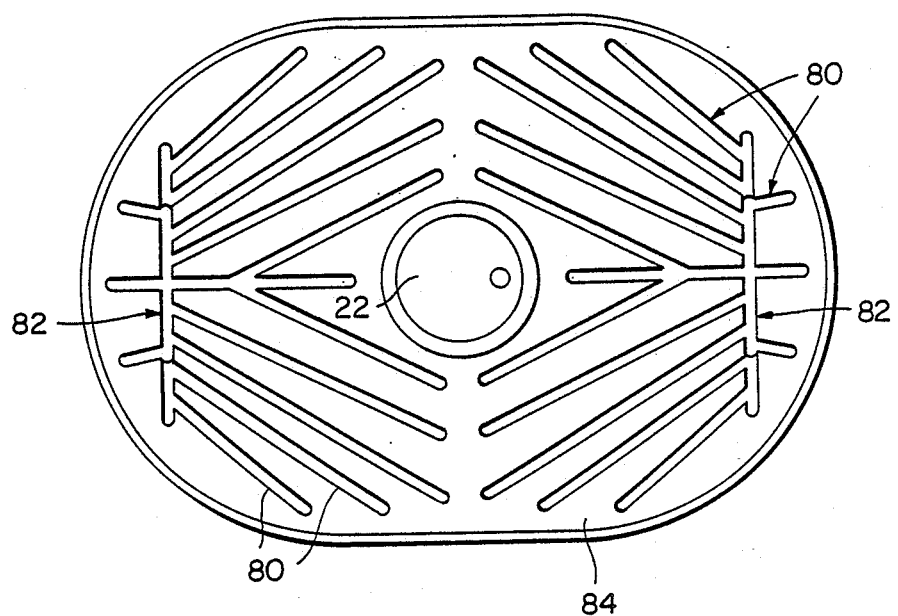
FIG. 3g is an underneath plan view of the electrode assembly with the cover partly removed.
Figure 3H:
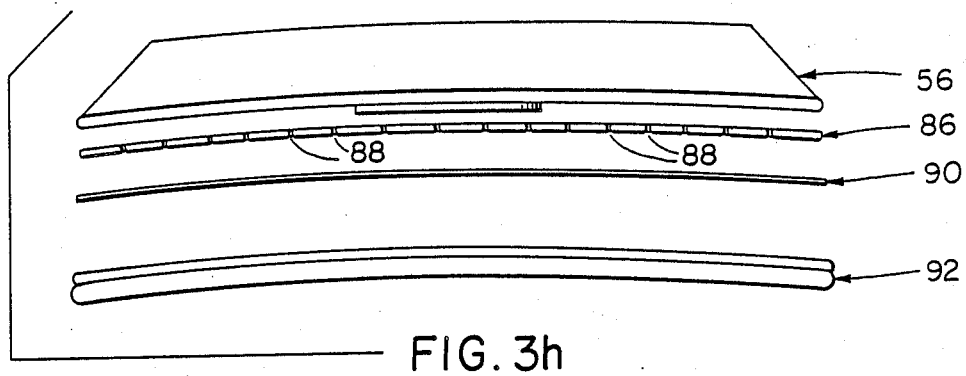
FIG. 3h is an exploded elevational view of parts of the electrode assembly.

Between the tubes 70 at each side of the electrode body, and attached to grooves in central housing 40, are opposite capsules 76 containing a conductive fluid such as an electrolyte gel. Central portions of the equalizer bars 66 surround the gel capsules such that when activated, the bars move along and compress the capsules and extrude the gel toward the ends of the electrode assembly away from central housing 40. Elongated ports 82 at the outer ends of the capsules 76 communicate with channels 80 in a base member 84 of the electrode body. FIG. 3g is a bottom view of the electrode assembly illustrating the gel channels 80 radiating from the capsule ports 82, and FIG. 3h is an illustration of the cross section of the skin-contacting surface. The gel channels are open along their length but base member 84 is covered by a restrictor plate 86 with restricted openings 88 which communicate with the respective channels.

The dimension of the gel channels are such that there is little impedance to the flow of conductive gel over the length of the channels, but the openings 88 impede the gel flow somewhat. This differential flow resistance ensures that upon activation of the extruder mechanism, the conductive gel rapidly fills all of the channels and then slowly the gel will be extruded through the holes in the restrictor plate. After passing through the plate, the gel then infiltrates a metallic mesh or perforated foil pulse electrode plate 90, which carries the current necessary for the electrical treatment, whether it be pacing, cardioverting or defibrillating. As the gel wets the metallic member, the electrical connection to the skin is enhanced by significantly lowering the impedance at the interface and providing a second form of impedance reducing means.

In the dry, non-activated state, a comfortably soft and absorbent fabric 92 covers plate 90 and contacts the patient's skin. This fabric typically is cotton. The fabric may be sewn through the surface of the electrode or may be loosely fitted onto the electrode with edges that curl over the electrode's edge and are held taut by an elastic member. This latter configuration allows frequent exchanges of the fabric surface for cleanliness purposes.

Figure 5A:
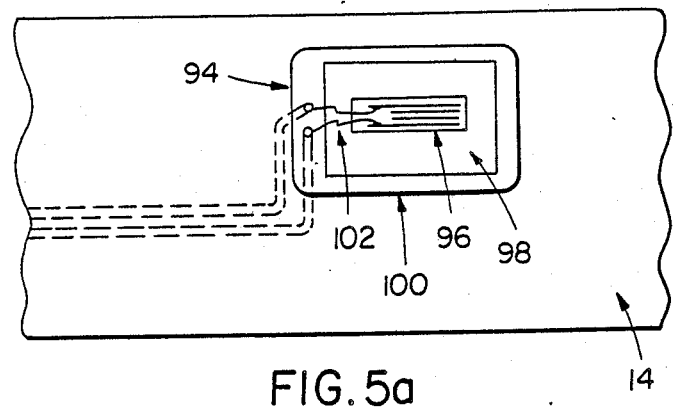
FIG. 5a is a diagrammatic plan view of a respiration sensor as used in the first embodiment pacemaker/defibrillator device.
Figure 5B:
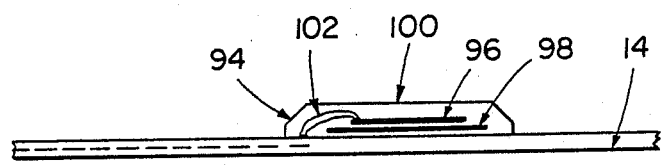
FIG. 5b is a diagrammatic elevational view of the respiration sensor.

FIGS. 5a and 5b illustrate a belt mechanism 94 which may be used to sense respiration movement. A strain gauge 96 is bonded to a metallic backing plate 98 which is attached firmly to belt 14. A protective molded cover 100 is applied over the gauge element which also encapsulates lead wires 102.

System operation will now be described with particular reference to FIG. 1.

A set of sensors (monitoring means) is used to gather information as to the patient's condition. The monitoring means include the respiration sensor 94, previously described, for detecting chest wall movement, the microphone 48 for picking up heart or respiration sounds, the ECG electrodes 22 to monitor the surface electrocardiogram and a reference ECG electrode 106 (known per se) to establish a "common" potential for electrodes 22. The signals from the sensors are amplified and conditioned by respective amplifiers 108, 110, 112 and a signal processing network 114. The conditioned signals are applied to a microprocessor 116.

The microprocessor, in conjunction with a system memory 118, performs all functions necessary for patient monitoring, time keeping and background operation, recording of arrhythmias and system events, communication with the maintenance subsystem 12, control of treatment sequences, self checks of system and electrode functioning, and monitoring of status switches 120 and 122. The microprocessor and memory together constitute essential elements of the pulse generator 24 described in connection with FIG. 4. These items are well known per se in heart treatment equipment and will not be described in further detail.

Also contained in the system memory 118, are tests and conditions for declaring a treatable event. When a treatable event is sensed, the microprocesor will initiate treatment as programmed in the system memory. Treatment modes and sequences may be individually personalized for each patient and may include low or high energy cardioversion/defibrillation, and a wide range of pacing modalities.

When a treatable event is sensed, the microprocessor activates the pressure means 124 (namely, the release mechanism 62 previously described) which pulls the pulsing electrodes 32 tightly against the patient's chest wall. Simultaneously, the electrode gel 126 is released by the treatment electrode as previously described to produce a low resistance contact. An impedance sensing circuit 128 is incorporated in the system to verify that the low resistance condition exists. At this point, the microprocessor may issue a spoken warning to stand clear via a voice synthesizer 130 and speakers 132, and causes treatment to begin through the pulsing electrodes, either pacing by a pacing circuit 134 or high energy shock by a defibrillator circuit 136. The patient, at his or her option, may delay treatment by simultaneously depressing two "live man" switches 120. If the patient'subsequently looses consciousness and releases the switches, treatment will begin; otherwise, the treatment is delayed.

Other functions which may be included in the system are an RF communications link to the maintenance system via receiver/transmitter 140 and antenna 142, and a power supply 144 which may have a rechargeable battery pack 146 to be charged by plugging into a charging port 148 on the maintenance system. An "on patient" sensor (switch 122) may be provided to inform the microprocessor that the device is in place on a patient. A self test feature may also be incorporated. Thus, by depressing one of the "live man" switches, the patient may initiate a test program which will report device status and/or any fault condition via speaker 132.

Figure 1:
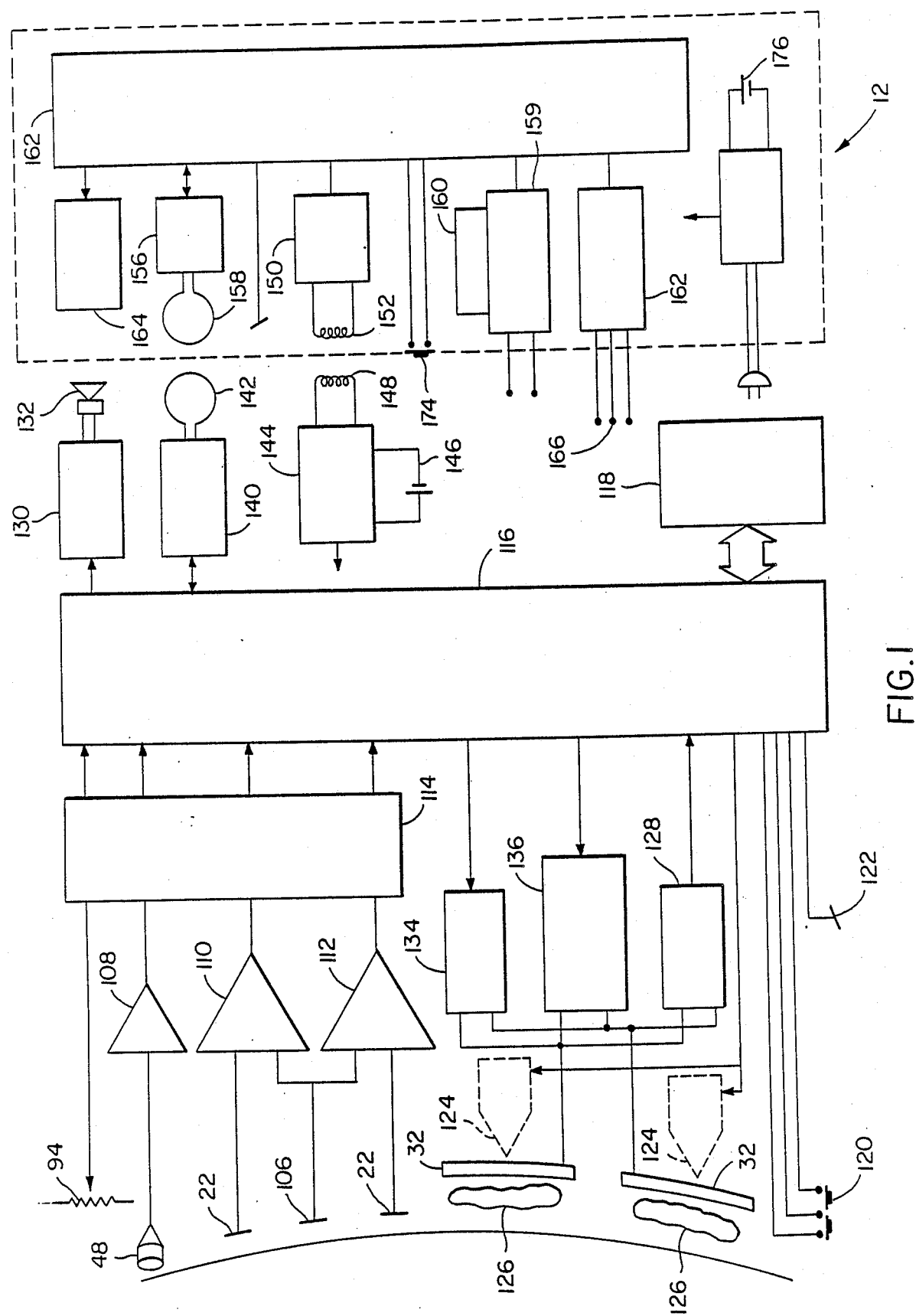
FIG. 1 is a block diagram of the functional elements of a first embodiment wearable automatic pacemaker/defibrillator device and maintenance subsystem for the wearable device.

The maintenance subsystem 12, a block diagram of which is shown on the right hand side of FIG. 1, may comprise a microprocessor-based support device for the belt device 10. The main functions of the maintenance subsystem are to provide a charger 150 for the belt power supply 144 and a communications link, for example between the belt and a telephone line. The charging may be effected either when the belt is on the maintenance device 12 using a built-in charging coil 152, or this coil may be extensible for remote use while the patient is wearing the belt. Alternatively, charging may be effected by alternating two battery packs. Communication with the belt is through an RF link 156 and an antenna 158. Communication with a telephone line is through a telephone dialer and modem 159 and a built-in speaker phone 160.

Other possible functions of the maintenance system will also be described. Thus, in FIG. 1, reference 162 is a microprocessor and system memory. The microprocessor controls all system functions. It also serves as the system clock with a time and status display 164. The system memory preferably is large compared with the belt memory, allowing it to store more of the patient's electrocardiogram and other data. The belt memory may be periodically "dumped" into the maintenance system for storage and eventual relay to a physician via telephone.

The maintenance system may also serve as a test system for the belt. For this purpose, test electrode outputs 166 (FIG. 6) may be located, such that when the belt is on the maintenance system, as determined by a sensor 168, the ECG test electrodes are in proximity to the belt pickup electrodes. Similarly, a respirator transducer 170 and a microphone test transducer 154 may be located near their corresponding sensors. This allows a full functional check of the belt sensing and detection mechanisms using test circuitry 162 (FIG. 1). This testing can be done automatically or initiated by the patient using a test button 174.

The maintenance system may be powered by an AC line and may incorporate a back-up battery 176 in case of a power outage. Other features may include power and charging status lights 178, a single button 180 for emergency dialing of a physician, allowing diagnosis and treatment by telephone during an emergency, and a built-in speaker phone 182 for convenience. A compartment 184 may be provided for charging coil storage.

The monitoring means may be adapted for detecting QRS electrical depolarization of the patient's heart and the patient's rate may be determined from the interval between QRS detections. Additionally, the rate of change of the patient's heart rate may be monitored. Also, or alternatively, the presence of an aortic valve closure sound may be used to verify or substitute for the sensing of a QRS electrical complex. A treatable tachycardia may be declared when the patient's heart rate exceeds a preset value for a preset time duration and the heart rate of change exceeds a preset level. A treatable bradycardia may be declared when the patient's heart rate drops below a preset rate for a preset time duration. Further, gasping motion or respiration may be used as a detection parameter for delivering a high-energy defibrillating shocks and may be used in combination with fast heart rate and/or fast heart rate acceleration for indicating the need for delivering of a high energy defibrillating shock.

As shown in FIGS. 7 and 8, a second embodiment heart therapy device 200, of similar functioning to the first embodiment device 10, may be worn with a comfortable, vest-like upper body garment structure 202, which may be form fitting and elasticized to ensure adequate contact of the sensing transducers with the skin surface, as will be described. The vest is constructed with sewn-in pockets 204 equipped with slide fasteners 206 or other positive-acting closures, into which electrode assemblies 208 of the device 200 are inserted prior to patient use, with pulse generator 210 of the device suitably attached to the vest and a conductor system 212 extending between the respective electrode assemblies and the pulse generator. It is understood that device 200 may be in the form of a self-contained treatment package with the conductors being contained in a suitable sheath 214 or the like which connects the various subassemblies. The device may also include a respiration sensor. The arrangement permits multiple vests to be on hand for cleanliness purposes, and allows the treatment package to be rapidly and easily changed between vests, ensuring relatively uninterrupted sensing and treatment.

The vest may additionally be fitted with appropriately located reinforcement sections, which upon receipt of a treatment-commencing signal from the pulse generator, translates movement of an upper half of the respective electrode housing into radial pressure against the patient's skin. As in the previous embodiment, the vest may have apertures allowing the respective electrode assemblies to contact the patient's skin. Additionally, the vest may have attachment means along its lower edge for attaching same to a belt, a lower body garment, or the like.

Figure 9A:
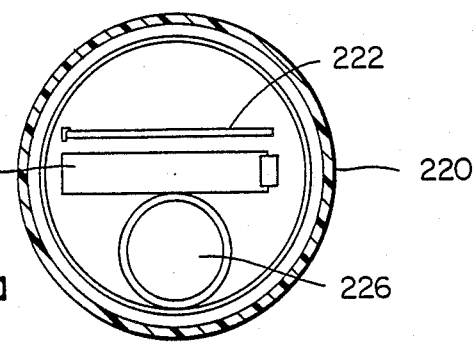
FIGS. 9a and 9b are sectional plan and sectional elevational views respectively of a sensing electrode assembly used in the second embodiment device.
Figure 9B:
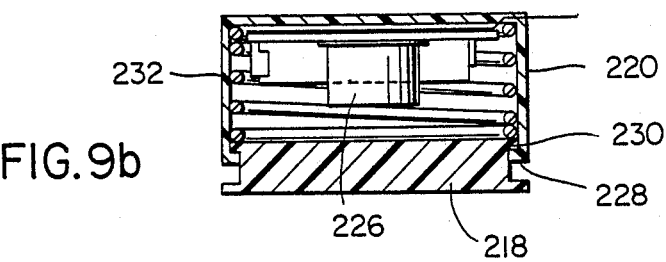

Each of the two ECG sensing/pulse delivery electrode assemblies 208 includes an ECG sensing electrode 218 (FIG. 9b) located within a plastic cylindrical housing 220, which is centrally located within the respective assembly 208. Electrode housing 220 contains the flexible, conductor-fiber-filled sensing electrode 218, two motion-detecting elements 222, 224, and associated amplifiers 226. The sensing electrode 218 is free to move vertically within the housing, but is limited in travel by molded-in bosses 228, 230. A spring 232 located beneath the chamber cover applies pressure to the top of the sensing electrode and thus to the patient's skin surface, ensuring constant contact between the ECG electrode surface and the skin whenever the system is worn.

Figure 10A:
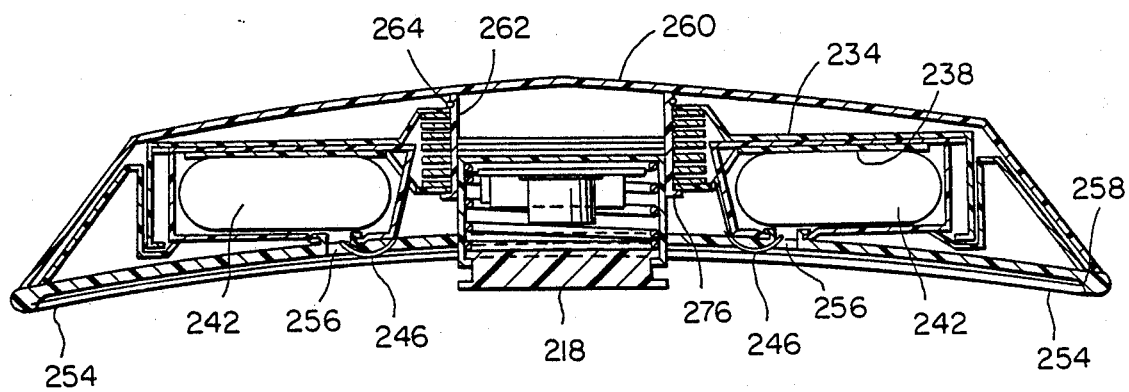
FIGS. 10a and 10b are sectional elevational views of a pulsing electrode assembly used in the second embodiment device, FIG. 10a showing the assembly in a holding mode, and FIG. 10b showing the assembly in an operational mode.
Figure 10B:
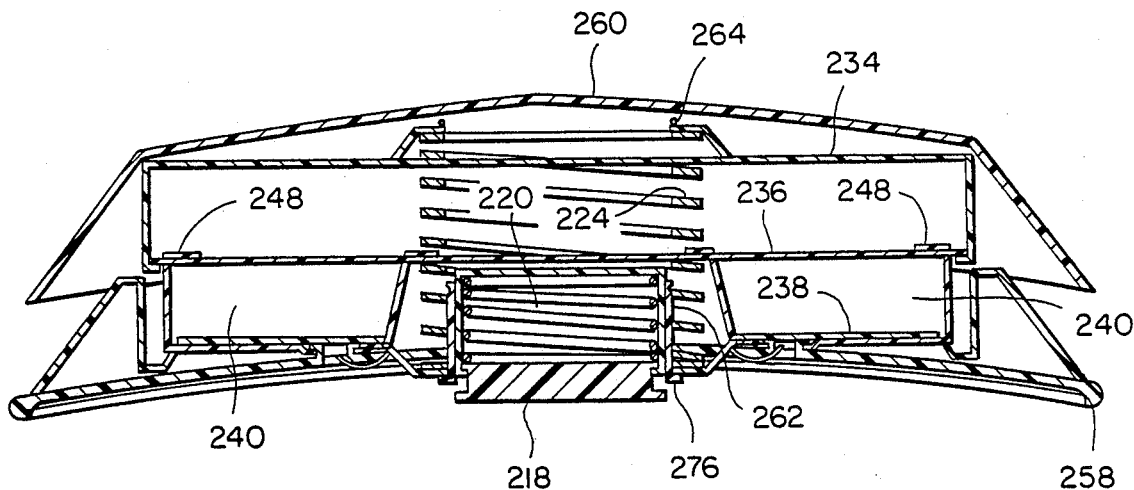
Figure 10C:
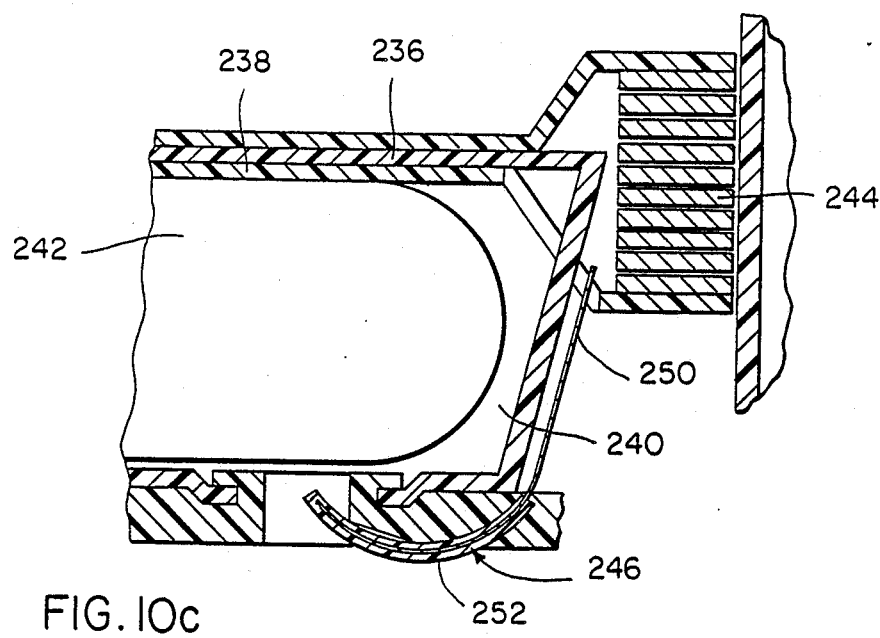
FIGS. 10c, 10d and 10e are enlarged sectional elevational views of parts of the pulsing electrode assembly when in the holding mode.
Figure 10D:
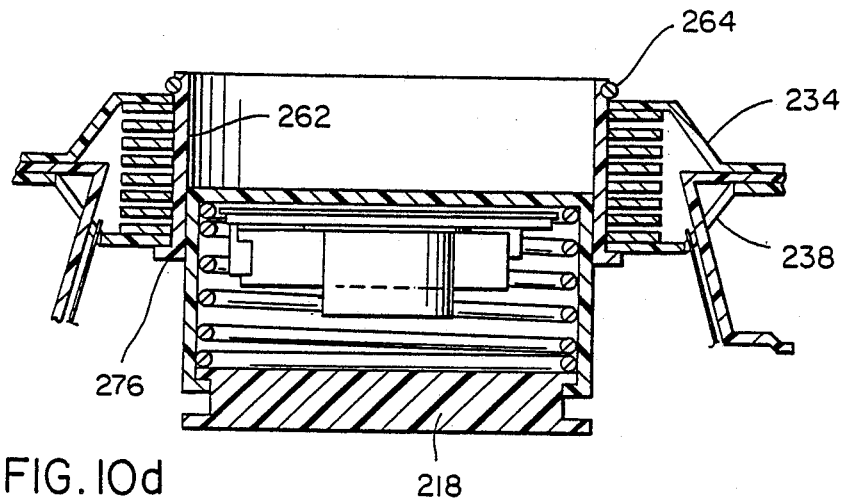
Figure 10E:
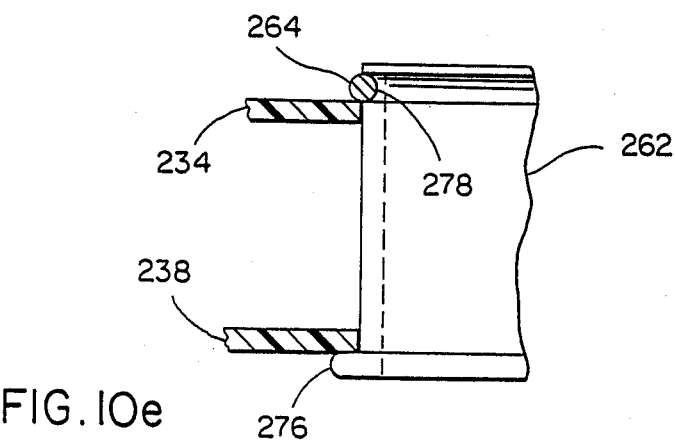
Figure 11A:
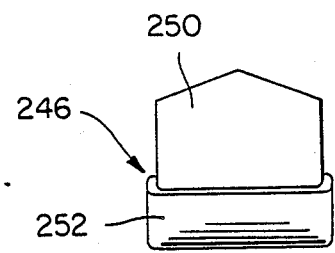
FIGS. 11a, 11b and 11c show respective parts of the puncture mechanism in the operational mode.
Figure 11B:
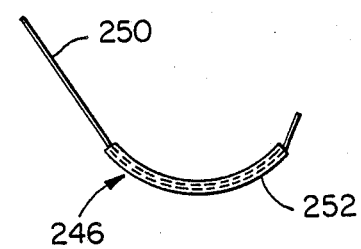
Figure 11C:
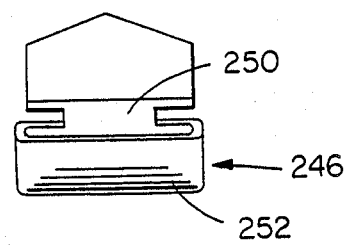
Figure 11D:
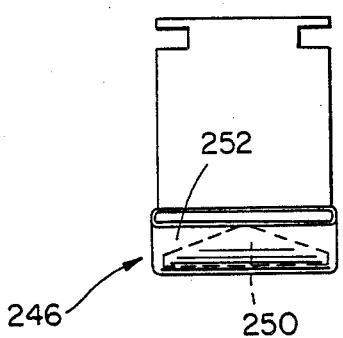
FIGS. 11d, 11e and 11f show the respective parts in the holding mode.
Figure 11E:
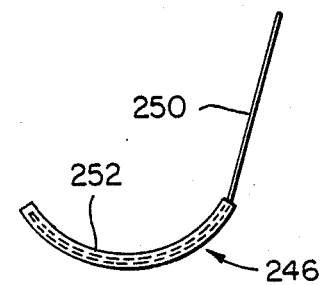
Figure 11F:
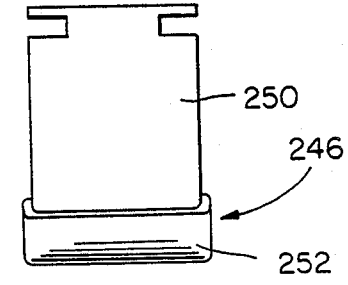
Figure 12:
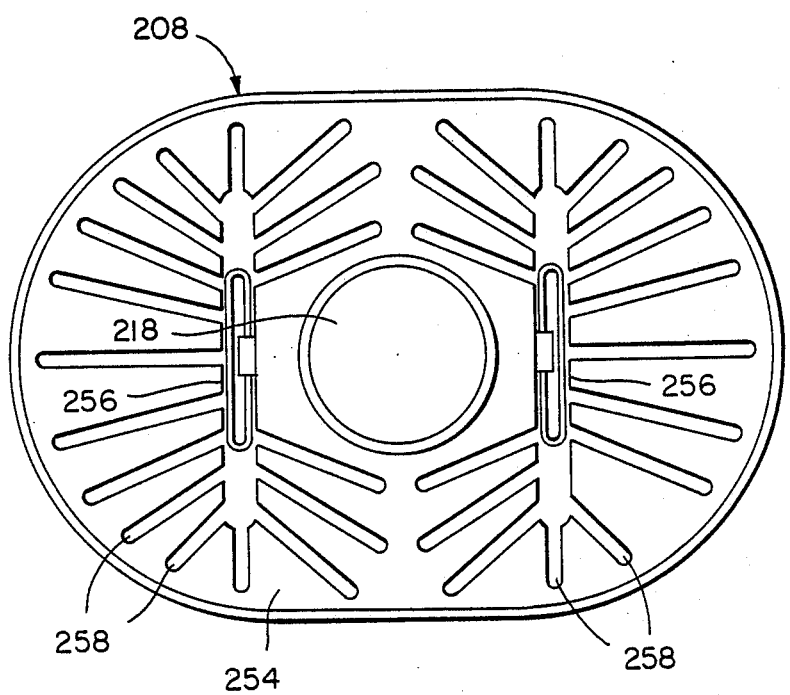

Each electrode assembly 208 additionally consists of a top plate 234 (see FIGS. 10a–10c), a housing cover 236, a compression plate 238, two U-shaped fluid container chambers 240, two conductive fluid-containing sacs or pouches 242, a compression spring 244, two puncture mechanisms 246, and a voltage controlled, heat operated release mechanism, to be described.

The chambers are permanently fastened to the housing cover with fold-over tabs 248. The compression plate 238 is installed beneath the housing cover 236, and between the compression plate and the bottoms of the chambers are situated the flexible sacs or pouches 242 containing the electrolyte or like conductive fluid.

Figure 13A:
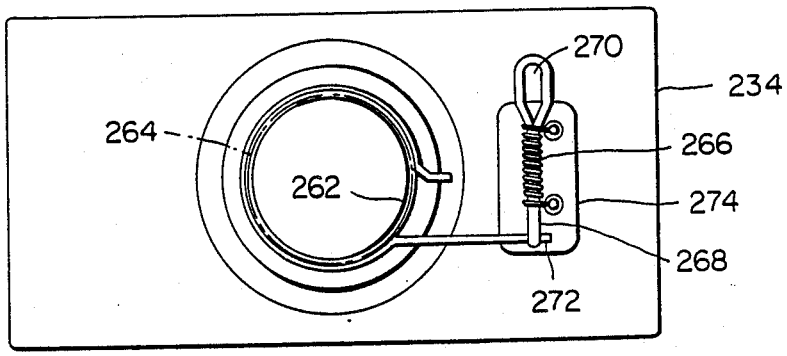
FIGS. 13a and 13b are respective plan views of a voltage controlled heat operated release mechanism, FIG. 13a being shown in the holding mode and FIG. 13b being shown in the operation mode.
Figure 13B:
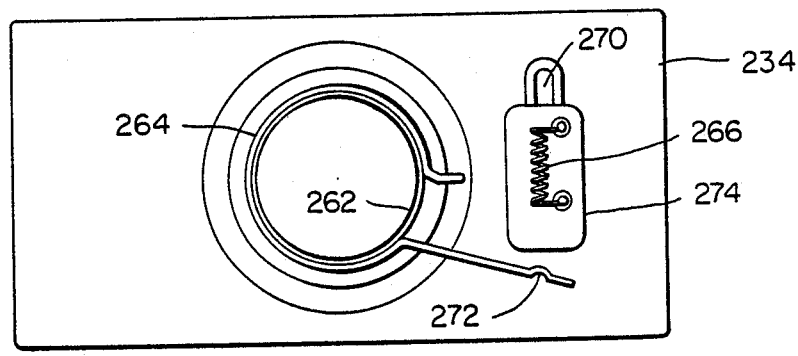

The plates 234 and 238 are held in close proxmity by a heat operated release mechanism, consisting of a cylindrical release sleeve 262, a torsion spring 264 located in a peripheral groove 278 at the upper end of the release sleeve, a resistance wire heating element 266, and a synthetic fiber restraining member 268 (see FIGS. 13a, 13b). Member 268 is fastened at one end to a pierced tab 270, or like fastener formed in top plate 234, and at the other end to a deformed zone in the torsion spring 272. An insulating strip 274 is installed under the heating element to isolate it from the top plate and to provide a means to make electrical connections to the element.

A flange 276 on the lower end of the release sleeve engages the underside of the compression plate 238 and the groove 278 on the upper end of the sleeve engages the torsion spring 264. The spring, (when compressed), engages the upper side of the top plate.

Upon receipt of the appropriate signal from the pulse generator 210, upon detection of a treatable heart condition, the heating element 266 melts through the restraining member 268, releasing the free end of the torsion spring 264, which disengages from the groove in the release sleeve, freeing the top plate.

The compression spring 244, applies pressure against the top plate 234, causing it to move upward, (away from the skin), and carry with it the top half of the electrode housing 260, to which it is fastened. This movement, via the enclosed pockets 204 in the vest structure, and the reinforcements sewn within the vest, transmits radial pressure against the chest wall, reducing the impedance at the electrode/skin interface, and ensuring adequate pressure for effective pulse delivery.

Additionally, the compression spring 244 applies downward pressure upon the compression plate 238 and the release sleeve 262, which are free to move toward the skin. This downward pressure is transmitted to the fluid sacs 242. The puncture mechanisms include pointed members 250 attached to the compression plate, which move through respective retaining tubes 252 and puncture the bottom surfaces of the fluid containers, when plates 234 and 238 are forced apart. As the compression plate moves through its travel, the fluid medium is forced out of the sacs into ports 256 and channels 254 situated in a bottom part of the electrode assembly, and by these means are transmitted to the pulsing electrode 258 and to the patient's skin surface, saturating this interface, and reducing the impedance thereby.

It will be apparent that electrode structures similar to structures 208 can also be employed in a harness-type garment which may include a belt, such as belt 14 and/or a shoulder strap, such as strap 18 as previously described.

In still another form of the invention, the impedance reducing mechanism may include a fluid-pressure actuated mechanism for increasing pressure of a pulse electrode against the patient's skin in response to a treatable heart condition being detected. Such fluid pressure actuated mechanism may include a gas cartridge for tightening an electrode-carrying belt or strap such as belt 14 or strap 18 previously described.

Figure 14:
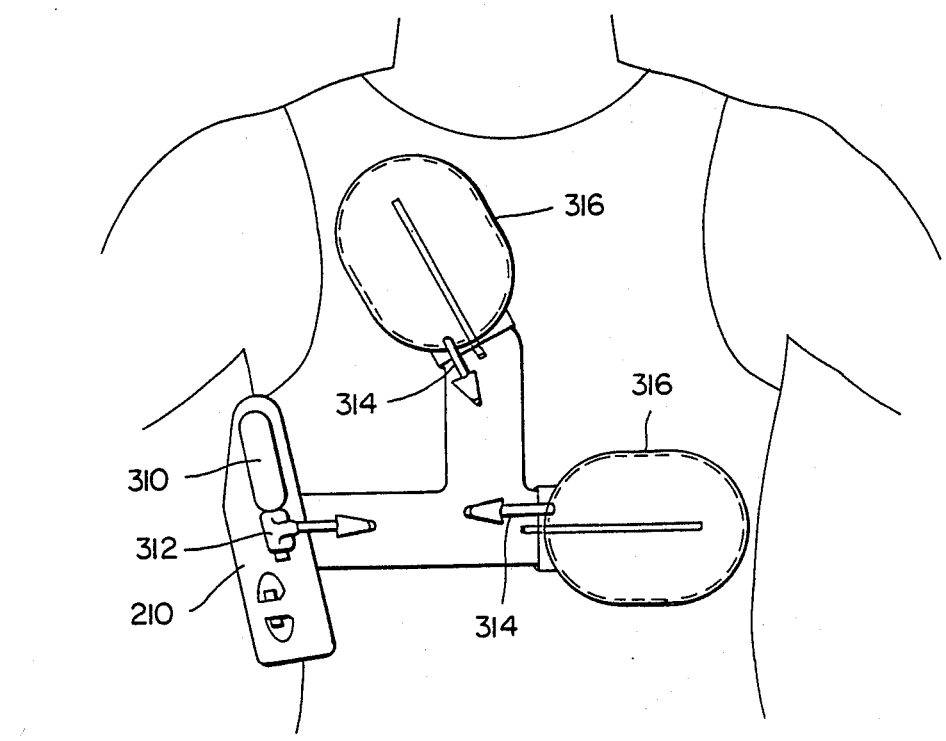
FIG. 14 is a diagrammatic in-use view of a third embodiment pacemake/defibrillator as worn by a patient.

One such embodiment consists of a gas source, (pressurized cylinder) 310, FIG. 14, and an electrically-operated actuator, or squib, 312, located on or near the pulse generator package 210, with conduits 314, for carrying gas under pressure to each electrode housing 316, upon activation of the gas source.

Figure 16A:
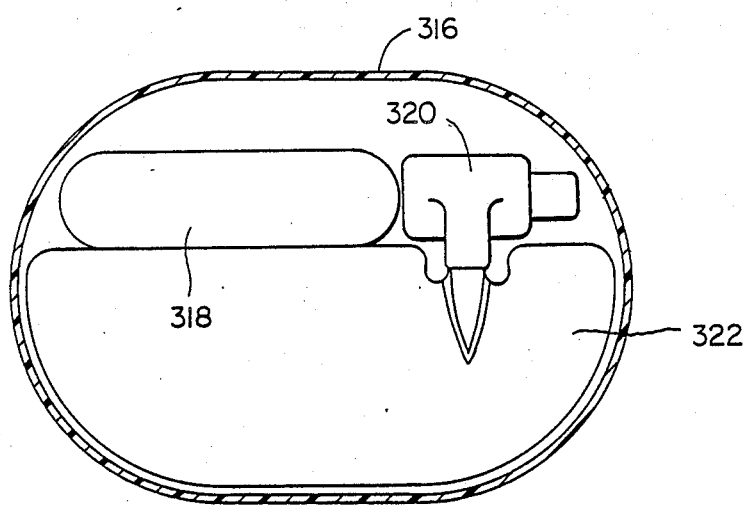
FIGS. 16a and 16b are respectively a plan view and an end view of the electrode housing with a gas source locally mounted within the pad housing.
Figure 16B:
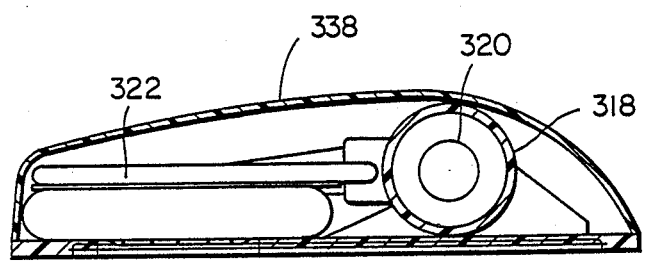
Figure 16C:
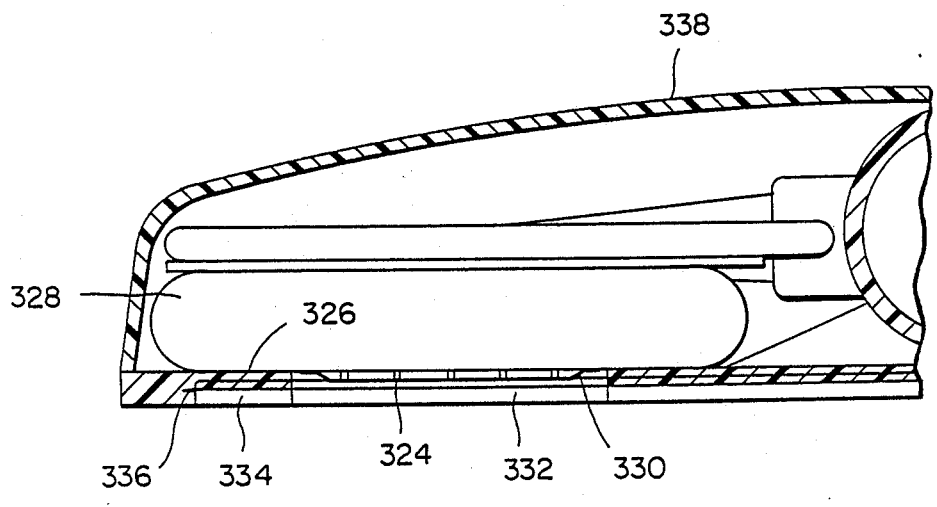
FIG. 16c is an enlarged end view showing increased detail of the electrode housing, including a fluid container, resistive heating element and retaining membrane.

A second such embodiment consists of a local gas source 318, and actuator 320, located in each electrode housing, as shown in FIGS. 16b and 16c.

In both such embodiments, each electrode may have an inflatable cell or bladder 322, (FIGS. 15 and 16) which at activation expands, supplying movement in two directions.

At detection, an electrical signal is sent to the gas actuator, releasing the gas from the respective gas source and pressurizing the inflatable cell.

A resistive heater 234, held in proximity to the lower wall 326, of the fluid sac 328, by a thermally bonded membrane 330, or other attachment means, heats when activated, melting through the wall of the sac and the membrane, thereby releasing electrolyte fluid or gel from the sac.

Pressure supplied by the inflated cell squeezes the fluid out of the sac and into ports 332, and channels 334, as in the previous embodiments saturating the skin contacting treatment electrode 336, and the skin surface.

The movement of the cell by expansion is simultaneously transmitted to the upper housing half 338, of the electrode assembly causing it to move upward, away from the skin. This movement, via an enclosed pocket 204 in the vest structure, and the reinforcements sewn within the vest or garment, transmits radial pressure against the chest wall, reducing the impedance at the electrode/skin interface.

The monitoring base station may be equipped with a known volumetrically controlled source of gas that can check the integrity of the inflatable cell or bladder by verifying the maintenance of pressure subsequent to test gas inflation by the monitoring system.

The vest/harness structure is designed to provide sufficient slack space to permit long term wearing comfort. The structure is initially fitted prior to day-to-day wear to ensure that this slack space is restricted to a dimension less than the combined electrode expansion distances, ensuring adequate pressure for effective pulse delivery.

While only preferred embodiments of the invention have been described herein and in detail, the invention is not limited thereby and modifications can be made within the scope of the attached claims.

What is claimed is:

1. A patient-worn device for automatically delivering electrical therapy to the heart upon the occurrence of a treatable heart arrhythmia, the device comprising: monitoring means for continuously sensing the patient's heart condition, skin-contacting treatment electrode means having a surface adapted for contact with the patient's skin, a source of electrical energy for supplying electrical pulses to the electrode means, discrimination means for receiving signals from the monitoring means and determining the presence of a treatable heart arrhythmia, impedance reducing means associated with the electrode means for actuation by the discrimination means responsive to the detection of a treatable heart arrhythmia for automatically reducing the impedance to electrical current flow at an interface between said surface of the electrode means and the patient's skin, and switching means actuated by the discrimination means responsive to the detection of a treatable arrhythmia for connecting the source of electrical energy to the electrode means thereby applying appropriate electrical pulses to the heart.

2. The invention as defined in claim 1 wherein the electrode means is mounted on carrier means in the form of an upper body harness or garment to be worn by the patient and the impedance reducing means includes means for tightening the carrier means about the patient.

3. The invention as defined in claim 1 wherein includes a source of electrically conductive fluid material and wherein the impedance reducing means includes means for releasing the electrically conductive material from said source and delivering same to said surface of the electrode means.

4. The invention as defined in claim 1 wherein the device is in the form of a body harness which includes a chest-encompassing belt and an over-the-shoulder strap, wherein the monitoring means includes at least one monitor on each of said belt and said strap, and wherein the electrode means includes at least one pulsing electrode on each of said belt and said strap.

5. The invention as defined in claim 4 in combination with an undergarment over which the device is to be worn, the undergarment including apertures for the monitors and electrodes.

6. The invention as defined in claim 4 wherein the harness comprises elastic material and is length-adjustable.

7. The invention as defined in claim 4 wherein the chest belt includes means for measuring chest movement of respiration.

8. The invention as defined in claim 1 wherein the device comprises a vest, a subassembly including the electrode means, the discrimination means and conductor means connecting the electrode means with the discrimination means, and means for releasably securing the subassembly on the vest.

9. The invention as defined in claim 8 wherein the means for releasably securing the subassembly on the vest includes pocket means in the vest for receiving and retaining the electrode means.

10. The invention as defined in claim 9 wherein the impedance reducing means includes means for expanding the electrode means within the pocket means for applying the electrode means with increased pressure against the patient's skin.

11. The invention as defined in claim 1 which includes signal generating means actuated by the discrimination means responsive to detection of a treatable arrhythmia for warning the patient, and a patient-activated switch means adapted to be activated by the patient for delaying the connection of the energy source to the electrode means.

12. The invention as defined in claim 11 wherein said switch means comprises two switches, both of which must be activated to delay such connection.

13. The invention as defined in claim 1 which includes an automatic voice signal generating means actuated by the discrimination means for advising the patient of information pertinent to the detection of a treatable arrhythmia.

14. The invention as defined in claim 13 wherein the generating means is adapted to deliver a warning of an impending high energy shock.

15. The invention as defined in claim 1 wherein the discriminating means includes memory for converting signals received from the monitoring means indicative of an excessively fast heart rate into a command for the energy source to supply high energy shock treatment to the heart through the electrode means.

16. The invention as defined in claim 1 wherein the discrimination means includes memory means for converting signals received from the monitoring means indicative of an excessively slow heart rate into a command for the energy source to supply pacing pulses to the heart through the electrode means.

17. The device as defined in claim 1 in combination with a maintenance subsystem having signal receiving and delivering means for interfacing with the monitoring means and the electrode means for providing at least one of the following functions, namely:
   a. automatic testing of the monitoring means with calibrated input signals;
   b. receiving data from a memory forming part of the discriminating means;
   c. testing and recharging of the source of electrical energy;
   d. transmitting memory data and sensed detection signals by telephone;
   e. allowing remote health care personnel to communicate by telephone with the patient to operate the patient-worn device; and
   f. serving as a high-volume memory storage element for patient and device data.

18. The invention as defined in claim 17 wherein the device comprises a carrier means in the form of an upper body harness or garment and the subsystem is in the form of a support for receipt of the carrier means thereon in a position such that the signal receiving and delivery means on the support registers with the monitoring means and electrode means on the harness.

19. An automatic system for applying electrical therapy to the heart, the system comprising: a patient-worn subsystem and a maintenance subsystem for the patient-worn subsystem, the patient-worn subsystem including skin-contacting monitoring means for continuously accessing the patient's heart condition, discrimination means including an electrical memory, for receiving signals from the monitoring means and determining the presence of a treatable heart arrhythmia from information stored in the memory, skin-contacting treatment electrode means having a surface adapted to contact the patient's skin, a source of electrical energy, and switching means actuated by the discrimination means for connecting the source of electrical energy to the patient's heart through the treatment electrode means in response to the detection of a treatable arrhythmia, the maintenance subsystem including means for interfacing with the monitoring means and electrode means when the patient worn subsystem is removed from a patient, means for testing operational status of the patient-worn subsystem and means for recording and storing contents of the memory of the patient-worn subsystem.

20. The system as defined in claim 19 wherein the patient-worn subsystem includes impedance reducing means actuated by the discrimination means for reducing impedance to electrical flow at an interface between the patient's skin and the electrode means responsive to detection of a treatable arrhythmia.

21. The system as defined in claim 19 wherein the maintenance subsystem includes means for transmitting data, such as the memory contents, and patient arrhythmia detection signals via telephone to a remote health care facility.

22. A patient-worn device for detecting a treatable heart arrhythmia and providing electrical treatment responsive thereto, the device being in the form of a body harness or vest which includes skin-contacting monitoring means adapted to contact a patient's skin for continuously monitoring heart rate, a source of electrical energy, skin-contacting electrode means adapted to contact the patient's skin, discrimination means for receiving signals from the monitoring means and comparing the signals with information in a memory to determine the presence of a treatable arrhythmia, switching means actuated by the discrimination means in response to determination of a treatable arrhythmia for connecting the source of electrical energy to the electrode means so as to apply appropriate electrical pacing to the heart, and impedance reducing means associated with the electrode means for actuation by the discrimination means in response to said determination for reducing impedance to electrical current flow at an interface of the patient's skin and the electrode means.

23. A device as defined in claim 22 wherein the discrimination means includes means for detecting heart rates below a preset value and the source of electrical energy includes means to apply pacing pulses to the electrode means for raising the heart rate.

24. The invention as defined in claim 22 wherein the discrimination means includes means for detecting heart rates above a preset value and the source of electrical energy includes means to apply a defibrillating pulse to the electrode means for effecting defibrillation.

25. The invention as defined in claim 22 wherein the body harness or vest includes tightening means for tightening same against the patient's skin, and a source of conductive fluid, and wherein the impedance reducing means includes means for applying the tightening means so as to increase pressure between the electrode means and the patient's skin, and the impedance reducing means further includes means for delivering the conductive fluid from the source to said interface.

26. The invention as defined in claim 25 wherein the impedance reducing means includes a common actuator means operated by the discrimination means for applying the tightening means and for delivering the conductive fluid.

27. The invention as defined in claim 26 including spring biasing means for urging the actuator means toward a tightening means-applying and conductive fluid-delivering position, restraining means for preventing the spring biasing means from urging the actuator means toward said position and trigger means operated by the discrimination means for releasing the restraining means.

28. The means as defined in claim 27 wherein the restraining means includes a heat destructable element and the trigger means includes heating means for destroying said element and thereby releasing the spring biasing means.

29. The invention as defined in claim 27, wherein the source comprises at least one squeezable fluid capsule and duct means connecting the capsule to a skin-contacting surface electrode means, and wherein the actuator means embraces the capsule for movement therealong by the spring biasing means so as to squeeze fluid from the capsule through the duct means.

30. The invention as defined in claim 27 including channel means in said surface of the electrode means for receiving fluid from the duct means.

31. The invention as defined in claim 27 wherein the actuator means includes plural actuators and the spring biasing means urges the actuators apart to apply a tightening force to the harness or vest.

32. The invention as defined in claim 22 in combination with a testing and servicing subsystem having signal receiving and delivery means adapted to interface with the monitoring means and electrode means, and microprocessing means for use in conjunction with the signal receiving and delivery means to provide servicing and testing functions for the device.

33. The invention as defined in claim 32 wherein the subsystem is contained in a stand for receiving the harness with the signal receiving and delivery means in registration with the monitoring means and electrode means.

34. The invention as defined in claim 22 wherein the electrode means is receivable with pocket means in the body harness or vest and wherein the impedance reducing means includes expander means for expanding the electrode means within the pocket means so as apply increased pressure against the patient's skin.

35. The invention as defined in claim 34 wherein the impedance reducing means further includes chamber means in the electrode means for a capsule of conductive fluid, conduit means leading from the chamber means to said interface and puncture means operated by the expander means for puncturing a capsule in the chamber means responsive to expansion of the electrode means.

36. The invention as defined in claim 35 wherein the electrode means includes a top plate, a compression plate forming an upper wall of the chamber means and a chamber base plate, wherein the puncture means is connected with the compression plate and wherein the expander means comprises an expansion spring for separating the top plate from the compression plate, thereby expanding the electrode means, causing the puncture means to puncture a capsule in the chamber means, and causing the capsule to be squeezed between the compression plate and the base plate so as to supply fluid to the interface through the conduit means.

37. An electrode assembly for use in a patient-worn body harness or vest for applying electrical energy pulses externally to the patient in the treatment of a heart arrhythmia, the assembly including a pulsing electrode having a skin-contacting surface adapted to contact the patient's skin, at least one squeezable capsule containing a conductive electrode fluid, duct means connecting said capsule to said surface of the electrode, a first actuator embracing the capsule, a second actuator, a spring-biasing means for urging the actuators apart, connectors for attaching the actuators to the harness whereby movement apart of the actuators by the spring biasing means provides a tightening force on the harness for increasing pressure between said surface and the patient's skin, and further provides movement of the first actuator along the capsule to squeeze fluid through the duct means and deliver same to the said surface, restraining means for preventing the spring biasing means from moving the actuators apart, and trigger means for releasing the restraining means.

38. The invention as defined in claim 37 including a second squeezable fluid capsule embraced by the second actuator, and further duct means connecting the second capsule to said surface of the electrode for the delivery of fluid thereto by movement of the second actuator along the fluid capsule.

39. The invention as defined in claim 38 including channels in the surface of the electrode for spreading fluid received through the duct means across said surface.

40. The invention as defined in claim 37 wherein the restraining means includes a heat destructable element and the trigger means includes a heater means for destroying said element.

41. The invention as defined in claim 37 including an aperture in said surface of the pulsing electrode and a sensing electrode located in said aperture.

42. An electrode assembly for use in a body harness or vest to be worn by a patient for applying electrical energy pulses externally to the patient in the treatment of a heart arrhythmia, the assembly including a pulsing electrode having a skin contacting surface adapted to contact the patient's skin, means defining a chamber within the assembly for a capsule of an electrically conducting fluid, the assembly having a cover portion remote from said skin contacting surface, a puncture means for puncturing a capsule within the chamber conduit means connecting the chamber with said skin contacting surface, pressure means for squeezing the capsule, and expander means for moving the cover portion away from said skin contacting surface, so as to increase the height of the assembly, while simultaneously operating the puncture means and the pressure means.

43. The invention as defined in claim 42 wherein the pressure means comprises a pressure plate forming an upper wall of the chamber and to which the puncture means is attached, and wherein the expander means comprises an expansion spring for separating the pressure plate and cover portion thereby increasing the height of the assembly while decreasing the height of the chamber and squeezing the capsule.

44. The invention as defined in claim 43 wherein the puncture means includes a curved needle carried by the pressure plate for puncturing the capsule from below on downward movement of the pressure plate.

45. The invention as defined in claim 42 in combination with a body harness or vest which includes pocket means for receipt of the assembly and pocket closure means for releasably encapsulating the assembly in the pocket means.

46. The invention as defined in claim 45 wherein the expander means comprises an expandable pneumatic chamber means within the electrode assembly and a source of fluid pressure for supplying fluid to said chamber means whereby the chamber means is expanded upon the detection of a treatable arrhythmia.

47. The invention as defined in claim 46 wherein said source is contained within the electrode assembly.

48. The invention as defined in claim 46 wherein said source is supported on a belt or harness adapted to be worn by the patient.

49. The invention as defined in claim 46 wherein the pneumatic chamber means has an expansion dimension sufficient to take up a maximum slack dimension of the vest or harness with a safety margin.

50. The invention as defined in claim 46 which includes a maintenance subsystem for use with the vest or harness, said maintenance subsystem including a pneumatic connection permitting periodic inflation of the chamber means to ensure correct harness adjustment, and adequate expansion and leak-tight integrity of the chamber means.

51. The invention as defined in claim 46 wherein the puncture means comprises means for heating a capsule in the chamber means so as to heat-rupture the capsule.

* * * * *